(12) United States Patent
Hirschman (10) Patent No.: US 7,067,139 B2
(45) Date of Patent: *Jun. 27, 2006

(54) METHOD FOR TREATING AUTOIMMUNE DISEASES

(75) Inventor: Shalom Z. Hirschman, Riverdale, NY (US)

(73) Assignee: Advanced Viral Research Corp., Yonkers, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 669 days.

(21) Appl. No.: 09/316,624

(22) Filed: May 21, 1999

(65) Prior Publication Data

US 2002/0013284 A1 Jan. 31, 2002

Related U.S. Application Data

(63) Continuation-in-part of application No. 08/735,236, filed on Oct. 22, 1996, now abandoned.

(51) Int. Cl.
*A61K 45/00* (2006.01)
*A61K 38/00* (2006.01)
*A61K 31/70* (2006.01)

(52) U.S. Cl. .................. 424/278.1; 424/195.1; 424/535; 424/548; 424/529; 514/2; 514/21; 514/44; 536/23.1

(58) Field of Classification Search .............. 424/278.1, 424/810, 529, 535, 548, 195.11; 514/2, 21, 514/8, 44, 45, 49, 825, 885; 536/23.1; 530/300
See application file for complete search history.

(56) References Cited

U.S. PATENT DOCUMENTS

| | | | | |
|---|---|---|---|---|
| 4,448,774 A | * | 5/1984 | Clemente et al. | 424/243 |
| 4,743,596 A | * | 5/1988 | Lapin | 514/161 |
| 5,807,839 A | * | 9/1998 | Hirschman | 514/44 |
| 5,807,840 A | * | 9/1998 | Hirschman | 514/44 |
| 5,849,196 A | * | 12/1998 | Kochel | 210/651 |
| 5,902,786 A | * | 5/1999 | Bregman | 514/2 |

OTHER PUBLICATIONS

Miller et al. 1992 Infectious Diseases, 5th edition, Chapter 3 pp. 15–29.*
Janeway–Travers 1997 ImmunoBiology, 3rd edition, Chapter 13, pp. 1–38.*
Reynolds, Margaret R., Generalized Vaccinia, Symposium, pp. 5–6, 1960.
Kuckku, Morris E., Herpetic Diseases, Symposium, pp. 7–13, 1960.
Schaeffer, Oden A., Influenza, Symposium, pp. 15–21, 1960.
Seydel, Frank, Epidemic, Asian Influenza, Symposium, pp. 23–24, 1960.
Cooke, Stanford B., Upper Respiratory Viral Manifestations, Clinical Symposium on Viral Diseases Demonstrating the Anti–viral Biotic Properties of the Drug Reticulose (Symposium), Sep., 1960, Miami Beach, Florida, pp. 25–32.
Medoff, Lawrence R., Infectious Mononucleosis, Symposium, pp. 33–37, 1960.
Anderson, Robert H., Encephalitis, Symposium, pp. 39–52, 1960.
Plucinski, Stanisloff J., Suspected Viral Varieties, Symposium, pp. 53–59, 1960.
Kosaka, K. and Shimada, Y., Infectious Hepatitis, Symposium, pp. 61–74, 1960.
Anderson, Robert H. and Thompson, Ralph M., Treatment of Viral Syndrome with a Lipoprotein–Nucleic Acid Compound (Reticulose), A Report of Five Cases, Virginia Medical Monthly, 84: 347–353, 1957.
Reynolds, Margaret R., Generalized Vaccinia Successfully Treated With Lipoprotein–Nucleic Acid Complex (Reticulose), Archives of Pediatrics, 77:421–422, 1960.
Wegryn, Stanley P., Marks, Robert A. and Baugh, John R., Herpes Gestationis, A Report of 2 Cases, American Journal of Obstetrics and Gynecology, 79:812–814, 1960.
Catterall, R.A., Lumpur, Kuala, A New Treatment of Herpes Zoster, Vaccinia And Chicken Pox, J. Roy. Coll. Gen. Practit., 1970, 19, 182.
Chinnici, Angelo A., Reticulose in Treatment Aids patients, Personal Communication to William Bregman, Jul. 6, 1992.
Cott, Rafael A., Summary of 11 Cases of Viral Infections Treated with Reticulose, Private Communication with Advance Viral Research Corp., 1989.
Cohen, Matthew, The Efficacy of a Peptide–Nucleic Acid Solution (Reticulose) for the Treatment of Hepatitis A and Hepatitis B—a Preliminary Controlled Human Clinical Trial, J. Roy. Soc. Health, Dec., 1992, 266–270.
Mundschenk, David D., In Vitro Antiviral Activity of Reticulose vs Influenaz A, Personal Communication with William Bregman, May 1, 1990.
Resnick, Lionel, Anti–HIV in Vitro Activity of Two Samples of Peptide–nucleic Acid Solution, Personal Communication with Dr. Bernard Friedland, Dec. 22, 1989.
Friedland, Bernard, In Vitro Antiviral Activity of a Peptide–Nucleic Acid Solution Against the Human Immunodeficiency Virus and Influenza A Virus, J. Roy. Soc. Health, Oct. 1991, 170–171.

(Continued)

*Primary Examiner*—Mary K. Zeman
*Assistant Examiner*—Lori A. Clow
(74) *Attorney, Agent, or Firm*—Jones Day (57) ABSTRACT

A method of treating patients having rheumatoid arthritis by administering Product R, a peptide-nucleic acid preparation, is disclosed.

4 Claims, 7 Drawing Sheets

OTHER PUBLICATIONS

Brazier, Anne D., Method for in Vitro Antiviral Evaluation Human Immunodeficiency Virus (HIV), Personal Communication with Dr. Bernard Friedland, Oct. 4, 1989.

Behbehani, Abbas M., Haberman Sol and Race, George J, The Effect of Reticulose on Viral Infections of Experimental Animals, Southern Medical Journal, Feb., 1962, 185–188.

Treatment of Viral Diseases with A Lipo–protein Nucleic Acid Complex (Reticulose)—A Clinical Study, Scientific Exhibit: Virginia State Medical Society Meeting, Washington D.C., Nov., 1957.

Kempe, Henry C., Fulginiti, Vincent A., and Vincent, Leone St., Failure to Demonstrate Antiviral Activity of Reticulose, Diseases of Children, vol. 103, No. 5, 655–657, 1962.

Sanders, Murray, Controlled Animal Studies with Reticulose Illustrating the Interference of Lipoprotein–Nucleic Acid Complex in the Experimental Animal Infected with Human Pathogenic Viral Entities, Southern Medical Association Scientific Exhibit, Dallas, Texas, Nov., 1961.

* cited by examiner

METHOD FOR TREATING AUTOIMMUNE DISEASES

CROSS REFRENCE AND RELATED APPLICATION

This is a continuation-in-part of application Ser. No. 08/838,073 filed on Apr. 15, 1997, entitled "A Method For Treating Autoimmune Diseases", now abandoned. Application Ser. No. 08/838,073 is herein incorporated by reference in its entirety.

BACKGROUND OF THE INVENTION

1. Field of the Invention

The present invention relates to a method for using Product R as hereinafter defined to treat patients having rheumatoid arthritis.

2. Description of the Related Art

Autoimmune diseases in mammals can generally be classified in one of two different categories: cell-mediated disease (i.e. T-cell) or antibody-mediated disorders. Non-limiting examples of cell-mediated autoimmune diseases include multiple sclerosis, rheumatoid arthritis, autoimmune tyroiditis, diabetes mellitus (Juvenile onset diabetes) and autoimmune uveoretinitis. Antibody-mediated autoimmune disorders include myasthenia gravis and systemic lupus erythematosus (or SLE).

Diseases with autoimmune features affect well over 5 percent of individuals at some time in their life. A large group of disparate autoimmune diseases are characterized by an often intense, sustained and injurious immune response apparently directed to a self-antigen. Autoimmunity is not a generalized state, but rather each disease reflects a highly specific pattern of recognition of different self structures and likely reflectsequally distinct immune recognition events. These disorders vary from relatively mild conditions to those that virulently attack critical cells and organs of the body.

Autoimmune diseases may be classified as organ specific or non-orgain specific depending on whether the response is primarily against either antigens localized to particular organs or widespread antigens. In organ specific diseases typified by Hashimoto's thyroiditis, lesions are restricted because the antigen in the organ acts a target for immunological attack. In non-organ specific disease typified by systemic lupus erythematosus (SLE), complexes formed with the antigens involved are deposited systemically, particularly in the kidney, joints and skin, so giving rise to the more diseminated features of the disease.

Systemic lupus erythematosus (SLE) is an inflammatory, multisystem disease characterized clinically as a relapsing disease of acute or insidious onset that may involve any organ in the body. Clinically, symptoms are due to disease affecting the skin, kidneys, serosal membranes, joints and heart. Anatomically, all sites have in common vascular lesions with fibrinoid deposits and immunologically, the disease involves antibodies of autoimmune origin, especially antinuclear antibodies (ANA). The ANA are directed against both DNA and RNA. Autoantibody development appears to be multifactorial in origin, involving genetic, hormonal, immunologic and environmental factors.

Rheumatoid arthritis is a systemic, chronic, inflammatory disease that affects principally the joints and sometimes many other organs and tissues throughout the body. The disease is characterized by a nonsuppurative proliferative synovitis, which in time leads to the destruction of articular cartilage and progressive disabling arthritis. The disease is caused by persistent and self-perpetuating inflammation resulting from immunologic processes taking place in the joints. As is the case with most autoimmune diseases the trigger that initiates the immune reaction remains unidentified. Both humoral and cell mediated immune responses are involved in the pathogenesis of rheumatoid arthritis. The majority of patients have elevated levels of serum immunoglobulins and essentially all patients have an antibody called rheumatoid factor (RF) directed against a component of another antibody class.

Multiple sclerosis is another disease that is thought to be caused by autoimmune mechanisms. The cause of multiple sclerosis is unknown but seems to be multifactorial. Susceptibility or resistance may be genetically determined; something in the environment interacts with the human host at the proper age to cause biochemical and structural lesions in the central nervous system. The systemic immune response and the response of the central nervous system become involved. Although the cause and pathogenesis of, multiple sclerosis are unknown, it is widely believed that immune abnormalities are somehow related to the disease. Three possible mechanisms have been postulated: infection, autoimmunity, and a combination of the two. Suppression or modulation of the immune responses may be the key.

Myasthenia gravis is an autoimmune disorder caused by antibodies directed against the acetylcholine receptor of skeletal muscle. Present information indicates at least three mechanisms whereby acetyicholine receptor antibody may interfere with neuromuscular transmission and thus induce myasthenia gravis. Acetylcholine receptor antibody pay interfere (directly or indirectly) with acetylcholine receptor function. In both experimental allergic myasthenia gravis and human myasthenia gravis, the extent of acetylcholine receptor loss parallels the clinical severity of the disease, suggesting that acetylcholine receptor antibody-induced acceleration of acetylcholine receptor degradation is important in the development of myasthenia gravis. Complement-mediated destruction of the postsynaptic region is the third possible cause. Other disorders, especially those presumed to be autoimmune in origin, can occur in association with myasthenia gravis. Thyroid disease, rheumatoid arthritis, systemic lupus erythematosus, and pernicious anemia all occur more commonly with myasthenia gravis than would be expected by chance.

Implication of viruses in auto immunity has been supported by findings that autoimmune responses are induced, accelerate or enhanced concomitant with infection by a wide variety of human DNA and RNA viruses. Using an investigative approach that focuses on one potential mechanism where microbes cause autoimmunity, or molecular mimicry, a number of etiologic agents have been identified as potential causes of autoimmune disease.

Certain viruses have a mitogenic effect on unique lymphocyte subsets and hence act as polyclonal activators. Viruses can also infect lymphocytes and macrophage and directly or through their proteins cause release of lymphokines and manikines. These molecules can modulate immune responses in a variety of ways, including as growth or differentiation factors or by regulating MHC class I and/or class II expression on cells. Finally, microbial agents share determinants with host self proteins. In this instance, an immune response mounted by the host against a specific determinant of the infecting agent may cross-react with the mimic (shared) host sequence, leading to autoimmunity and, in some cases, tissue injury and disease.

The current treatments for both categories of autoimmune diseases involve administration of drugs which nonspecifically suppress the immune response. Examples of such drugs are methotrexate, cyclophosphamide, Imuran (azathioprine) and cyclosporin A., steroid compounds such as prednisone and methylprednisilone are also employed in many instances. These drugs have limited efficacy against both cell- and antibody-mediated autoimmune diseases. Use of such drugs is limited by virtue of their toxic side effects and also because they induce "global" immunosuppression in a patient receiving prolonged treatment with the drug, e.g. the normal protective immune response to pathogenic microorganisms is downregulated thereby increasing the risk of infections caused by these pathogens. A further drawback is that there is an increased risk that malignancies will develop in patients receiving prolonged global immunosuppression.

Reticulose® emerged as an antiviral product in the 1930's. While it was originally believed to be a product composed of peptone, peptides and nucleic acids, the precise composition remains unidentified. Nevertheless, Reticulose® has demonstrated an ability to inhibit rapidly the course of several viral diseases. It is nontoxic, miscible with tissue fluids and blood sera and free from anaphylactogenic properties. Product R is a refinement of Reticulose® prepared by an improved manufacturing process. It is a peptide nucleic acid preparation with defined composition.

Insofar as the applicant knows, Product R has never been used, nor suggested for treating autoimmune diseases.

SUMMARY OF THE INVENTION

An object of this invention therefore is to provide a method for treating a patient having autoimmune diseases by administering parenterally an effective treatment amount of Product R, a peptide-nucleic acid preparation, to the patient.

Product R is particularly useful in treating patients identified as having autoimmune disease rheumatoid arthritis.

Specifically, Product R is administered parenterally to the patients in a range from about 2.5 microliter to about 40 microliter per kilogram of the patient's body weight per day in a sterile injectable formulation. Prednisone may be co-administered with Product R to the patients orally in a range from about 0.065 to about 1.35 milligram per kilogram of the patient's body weight per day.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE PRESENTLY PREFERRED EMBODIMENTS

As used herein, Product R is the product according to either of the following methods.

Method I For Preparing Product R

Suspend about 35.0g of casein, about 17.1g of beef peptone, about 22.0g of nucleic acid (RNA), about 3.25g bovine serum albumin in about 2.5 liters of water for injection USP at about 3 to 7° C. in a suitable container and gently stir until all the ingredients have been properly wet. Carefully add while stirring about 16.5g of sodium hydroxide (reagent grade ACS) and continue stirring until sodium hydroxide completely dissolved. Autoclave at about 9 lbs pressure and 200–230° F. for a period of time until RNA is completely digested, for example, about 4 hours. At the end of the period, the autoclave is stopped and the reaction flask and contents are permitted to slowly cool to ambient temperature. Then cool for at least six hours at about 3–8° C. The resulting solution is filtered through 2 micron and 0.45 micron filters using inert gas such as nitrogen or argon at low pressure (1–6 psi). In a similar manner the solution is filtered again through 0.2 micron pyrogen retention filters. The resulting filtrate is sampled and assayed for total nitrogen. A calculation is then performed to determine the quantity of cooled water for injection to be added to the filtrate to yield a diluted filtrate with a nitrogen content between about 165–210 mg/ml, the final volume is approximately 5 liters. The pH is then adjusted with either concentrated HCl (reagent grade ACS) or 1.0 normal NaOH to about 7.3–7.6 range. The diluted solution is then filtered again through 0.2 micron filters with inert gas at low pressure. The final filtrate is then filled and sealed into 2ml glass ampules while in an inert gas atmosphere. The ampules are collected and autoclave for final sterilization at 240° F. and 20 to 30 pounds pressure for about 30 minutes. Following the sterilization cycle, the ampules with Product R are cooled and washed.

All quantities are subject to plus or minus 2.5% variation for pH, volume, and analytical adjustments.

Method II For Preparing Product R

Suspend about 35.0g of casein, about 17.1g of beef peptone, about 22.0g of nucleic acid (RNA), about 3.25g bovine serum albumin in about 2.5 liters of water for injection USP at about 3 to 7° C. in a suitable container and gently stir until all the ingredients have been properly wet. Slowly add while stirring about 11.75 ml of hydrochloric acid (reagent grade ACS) and continue stirring until hydrochloric acid is completely dissolved. Autoclave at about 9 lbs pressure and 200–230° F. for a period of time until RNA is completely digested, for example, about 4 hours. At the end of the period, the autoclave is stopped and the reaction flask and contents are permitted to slowly cool to ambient temperature. Then cool for at least six hours at about 3–8° C. The resulting solution is filtered through 2 micron and 0.45 micron filters using inert gas such as nitrogen or argon at low pressure (1–6 psi). In a similar manner the solution is filtered again through 0.2 micron pyrogen retention filters. The resulting filtrate is sampled and assayed for total nitrogen. A calculation is then performed to determine the quantity of cooled water for injection to be added to the filtrate to yield a diluted filtrate with a nitrogen content between about 165–210 mg/ml, the final volume is approximately 5 liters. The pH is then adjusted with either concentrated HCL (reagent grade ACS) or 35% (w/v) of NaOH to about 7.3–7.6 range. The diluted solution is then filtered again through 0.2 micron filters with inert gas at low pressure. The final filtrate is then filled and sealed into 2 ml glass ampules while in an inert gas atmosphere. The ampules are collected and autoclave for final sterilization at 240° F. and 20 to 30 pounds pressure for about 30 minutes. Following the sterilization cycle, the ampules with Product R are cooled and washed.

All quantities are subject to plus or minus 0.5% variation for pH, volume, and analytical adjustments.

Product R may be administered alone or together with an autoimmune disease treatment agent. When administered to the patients, Product R may be applied parenterally, the autoimmune disease treatment agent, e.g. prednisone may be administered orally. The combination of Product R and prednisone may be applied either simultaneously or in alternation.

For the above autoimmune diseases, a suitable effective dose of Product R is in the range from about 2.5 microliter to about 40 microliter per kilogram of body weight per day, preferably in the range of about 5 microliter to about 25 microliter per kilogram of body weight per day. Most preferably Product R is administered in an amount of about 7.5 microliter per kilogram of body weight per day. The desired dose may be administered as two, three or more sub-doses at appropriate intervals, generally equally spread in time, throughout the day. Preferably, however, the full daily dose is administered in one administration.

Product R may be administered by any suitable injection route including, but not limited to intravenously, intraperitoneal, subcutaneously, intramuscularly, and intradermally, etc. The presently preferred route of administration is intramuscularly. It will be appreciated that the preferred route may vary with, for example, the condition and age of the recipient.

While it is possible for Product R to be administered as part of a pharmaceutical formulation, it is preferable to present it alone, although it may be administered at about the same time as one or more other pharmaceuticals are independently administered. If Product R is administered as part of a pharmaceutical formulation, the formulations of the present invention comprise at least one administered ingredient, as above defined, together with one or more acceptable carriers thereof and optionally other therapeutic ingredients. The carrier(s) must be "acceptable" in the sense of being compatible with the other ingredients of the formulation and not deleterious to the recipient thereof. Preferably, Product R constitutes at least about 90% of such formulation by.

The formulations may conveniently be presented in unit-dose or multi-dose containers, e.g. sealed ampules and vials.

Preferred unit dosage formulations are those containing a daily dose or unit, daily sub-dose, or an appropriate fraction of the administered ingredient.

Prednisone may be co-administered with Product R to provide a combined therapy in treating autoimmune diseases. While it is possible for the active ingredients of prednisone to be administered alone, it is preferable to present them as pharmaceutical formulations. The formulations comprise at least one active ingredient, together with one or more acceptable carriers therefore and optionally other therapeutic ingredients. The carrier(s) must be "acceptable" in the sense of being compatible with the other ingredients of the formulation and not deleterious to the patient thereof.

The formulations for prednisone includes those suitable for oral administration. The formulations may conveniently be presented in unit dosage form and may be prepared by any of the methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers of finely divided solid carriers or both, and then, if necessary, shaping the products.

For oral administration, prednisone is calculated as the free base of about 0.065 to 1.35 milligram per kilogram, preferably 0.25 to 0.8 milligram per kilogram, of the patient's body weight per day, and is preferably used in a unit dosage form, and administered a few times daily in the amount of 1 to 50 milligram per unit dose. Dosage of prednisone should be individualized according to the severity of the disease and the response of the patient.

It should be understood that Product R may also be co-administered with other anti-autoimmune disease agents such as methotrexate, cyclophosphamide, imuran and cyclosporin A, etc. The dose of other anti-autoimmune disease agents to be co-administered with Product R can be readily determined by those skilled in the art, based on the usual patient symptoms, and severity of the diseases.

A clinical trial to assess the efficacy of Product R in patients suffering from rheumatoid arthritis (RA) has been conducted under a designed by applicant. In this clinical study, twenty-seven female patients ranging in age from 29 to 50 years old, suffering from mild to moderately severe RA for no longer than two years were treated with Product R for a total of 90 days. These patients had been previously treated with Aspirin and/or Paracetamol and /or Arrumalon. Product R was injected subcutaneously at a dose of 1 ml twice per day for 15 days and 1 ml once a day for 75 days. One additional patient, 44 years old, afflicted with severe RA manifested as decrease in articular space, osteopenia ,and subchondral sclerosis, who was previously treated with gold salts but discontinued due to toxic effects, was injected subcutaneously with Product R at a dose of 2 ml once per day for the first three days followed by 1 ml once per day for 12 months. Two other patients who had suffered from HA for seven and three years respectively where injected subcutaneously with 2 ml of Product R every other day for 15 days, 2 ml every other day for 15 more days and for the next year they were given a maintenance dose of 1 ml a day for 5 consecutive days every 4 months.

No major or minor side effects were observed or reported. Only one patient reported, on day 90, a mild reaction at the site of injection that lasted two days and resolved by itself.

The improvement of rheumatoid arthritis were determined according to measurements such as pain, tumefaction of soft tissues, morning stiffness, mobility of the most affected joint, the size of the most affected joint and same laboratory tests.

Figure 1A:
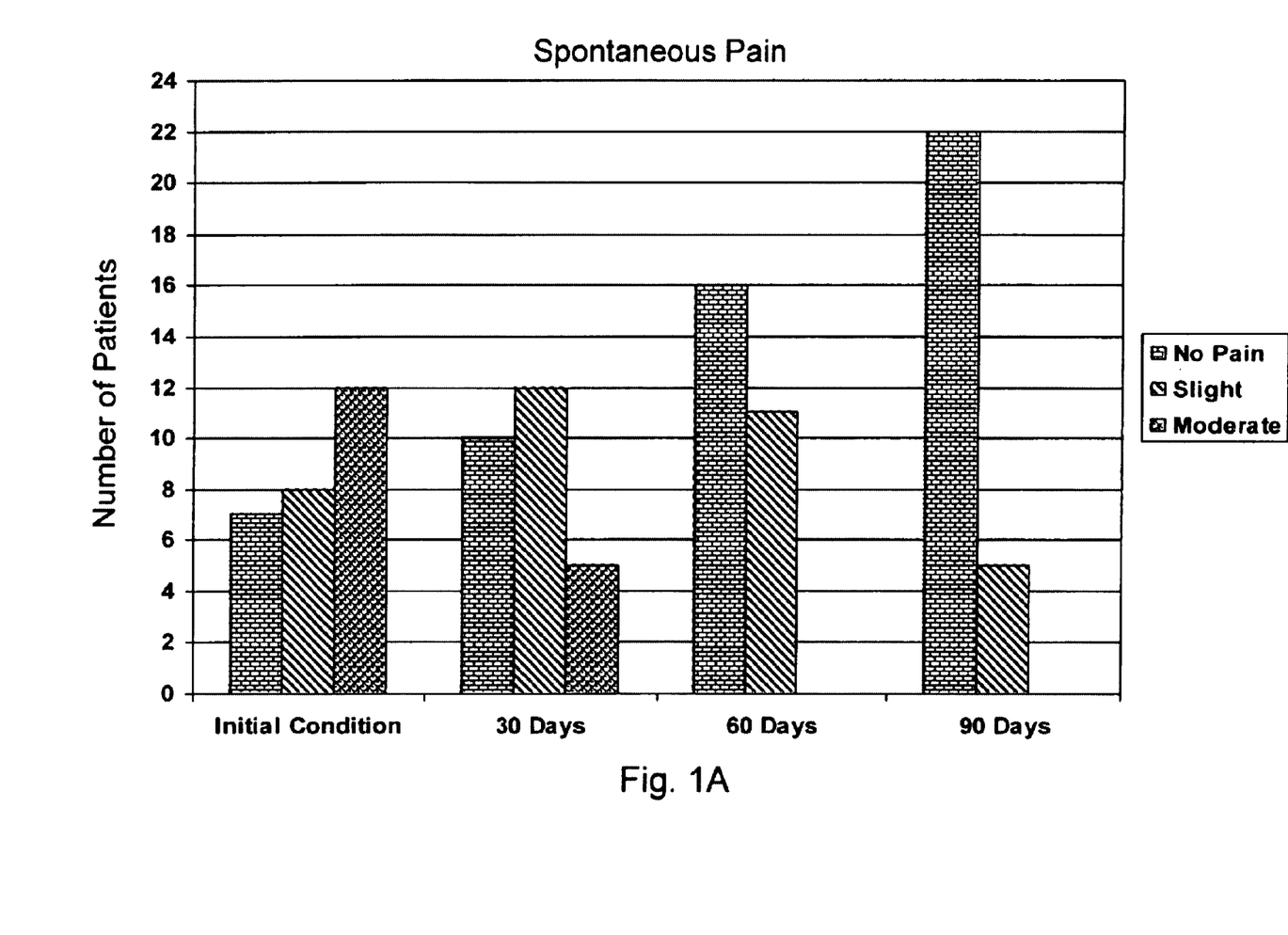
FIG. 1A shows the reduction of spontaneous pain resulting from the treatment with Product R.

FIG. 1A shows the reduction of spontaneous pain resulted from the treatment with Product R. Prior to the treatment, of twenty-seven patients, seven reported no pain, eight reported slight pain, and twelve reported moderated pain, which are represented by the shaded bars. By day thirty of the treatment, five patients reported moderate pain and twelve patients reported slight pain. By day sixty, eleven patients had slight pain. By day ninety, only 5 patients still reported slight pain. The severe RA patient was monitored on days 0, 15, 30 and 45 of the treatment. By day 45, she still experienced moderate spontaneous pain.

Figure 1B:
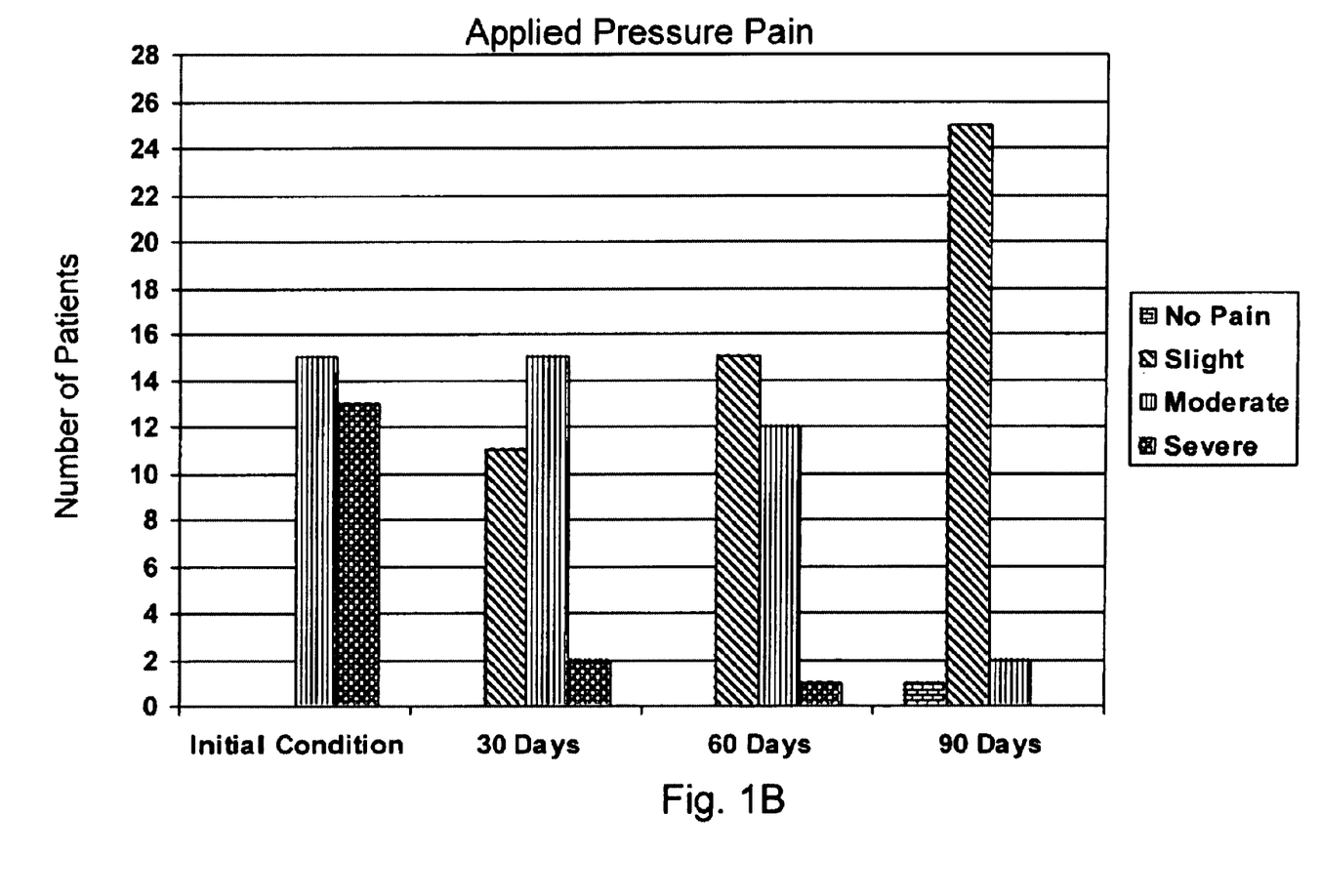
FIG. 1B shows the reduction of the applied pressure pain resulting from the treatment with Product R.

FIG. 1B shows the reduction of the pain produced by applied pressure. All twenty eight patients including the severe RA patient reported moderate (fifteen patients) to severe (thirteen patient) pain before the treatment. By day thirty of the treatment, eleven reported slight pain, fifteen moderate pain and two severe pain. By day sixty, fifteen patients had slight pain and thirteen reported moderate pain. By day ninety, one patient had no pain, twenty five slight pain and two moderate pain.

Figure 1C:
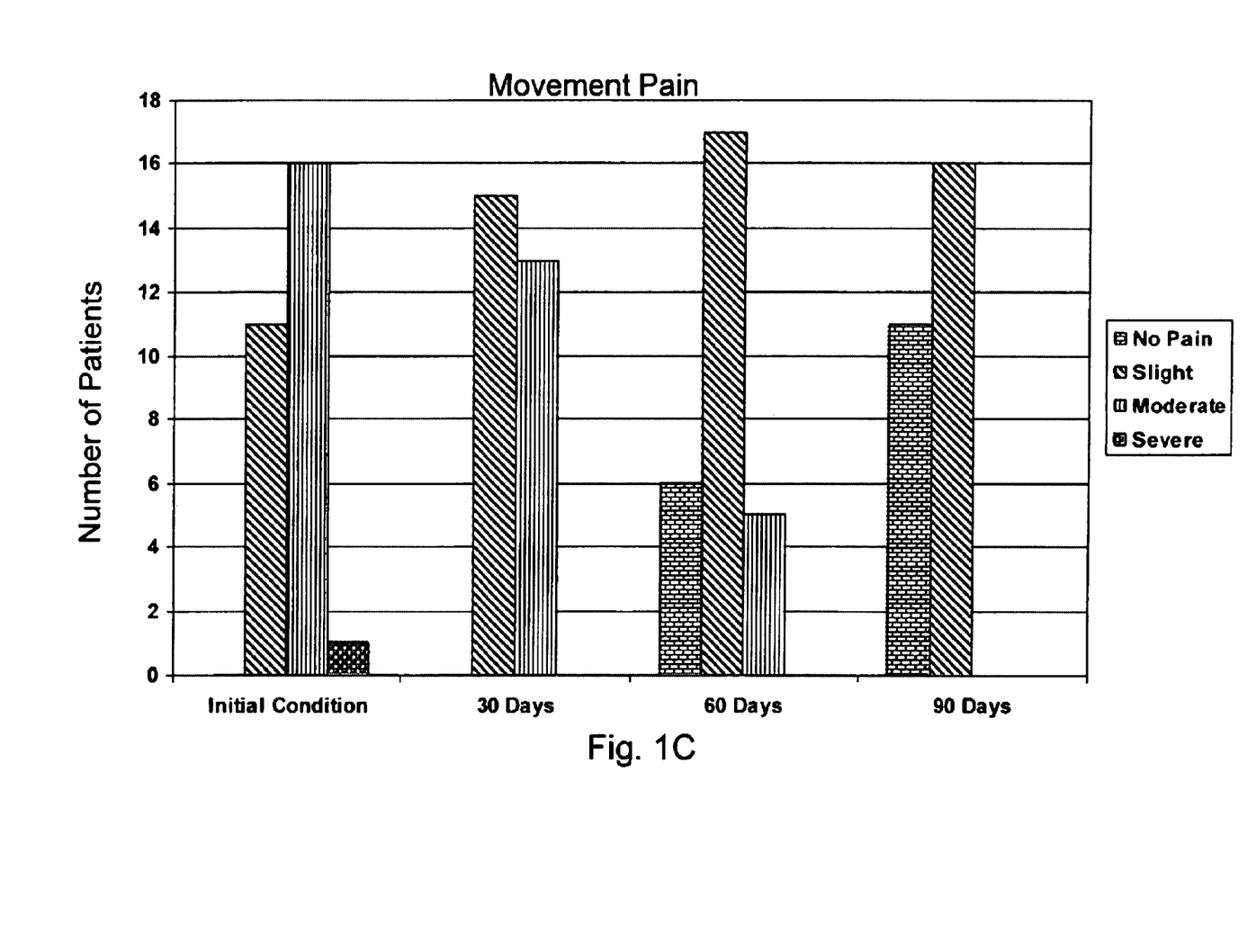
FIG. 1C shows the reduction of the movement pain resulting from the treatment with Product R.

FIG. 1C shows the reduction of the pain produced by movements. All 28 patients reported pain produced by movement before the including 11 suffering from slight pain, 16 moderate pain and one severe pain (the severe RA patient). By day 30 of the treatment, 15 reported slight pain, 12 had moderate pain and one had severe pain. By day 60, 6 had no pain, 17 had slight pain and 5 had moderate pain. By day 90, 11 had no pain, 16 had slight pain and one had moderate pain.

Figure 2:
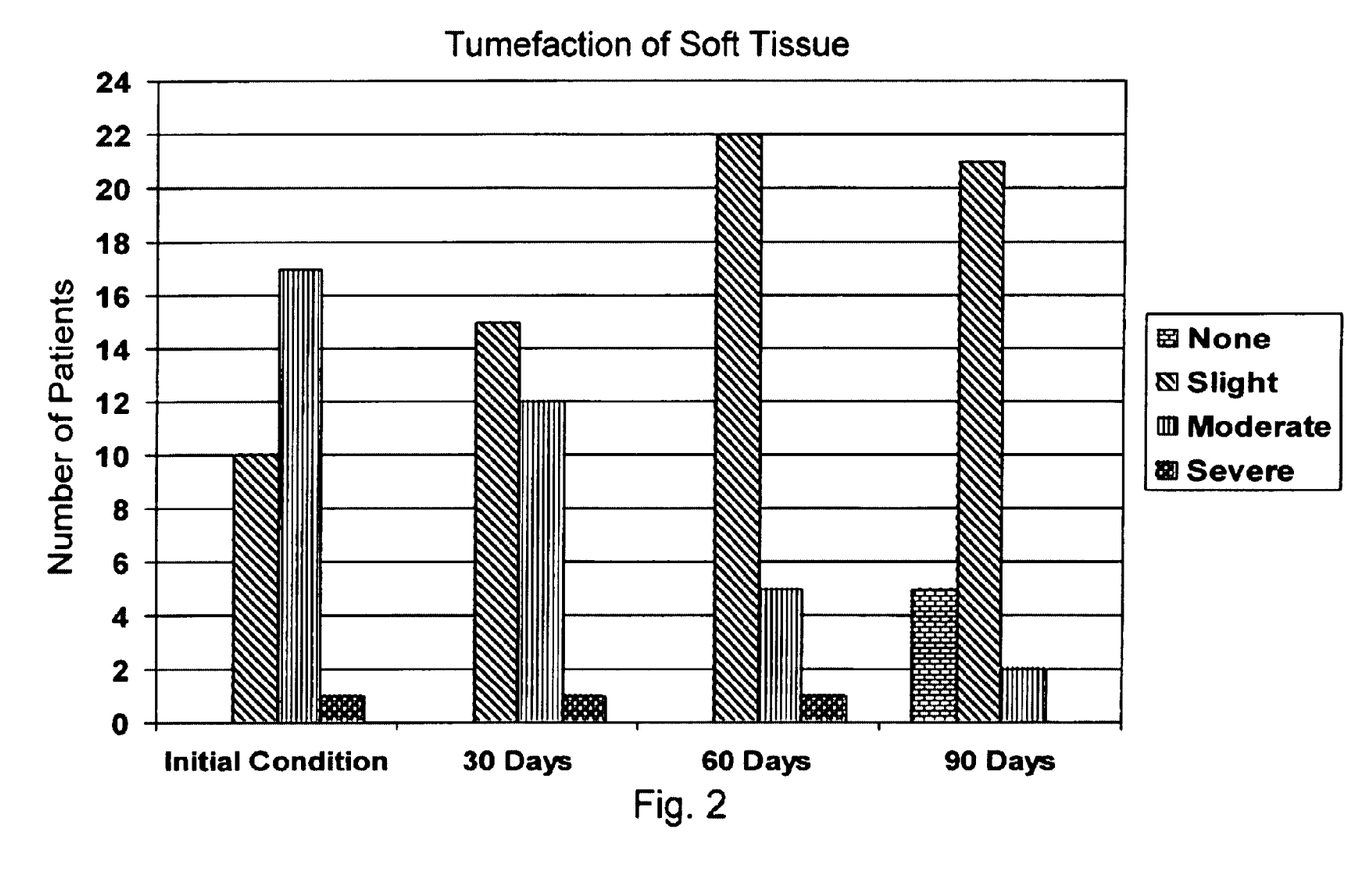
FIG. 2 shows the reduction of tumefaction of soft tissues resulting from the treatment with Product R..

FIG. 2 shows the reduction of tumefaction of soft tissues. All 28 patients had some degree of tumefaction (swell) of soft tissue before the treatment including 10 slight, 17 moderate and one severe tumefaction. By day 30, 5 patients having moderate tumefaction reported slight tumefaction. By day 60, seven more patients changed form moderate to slight tumefaction. By day 90, five patients had complete disappearance of tumefaction, 21 had slight tumefaction and two remained with moderate tumefaction.

Figure 3:
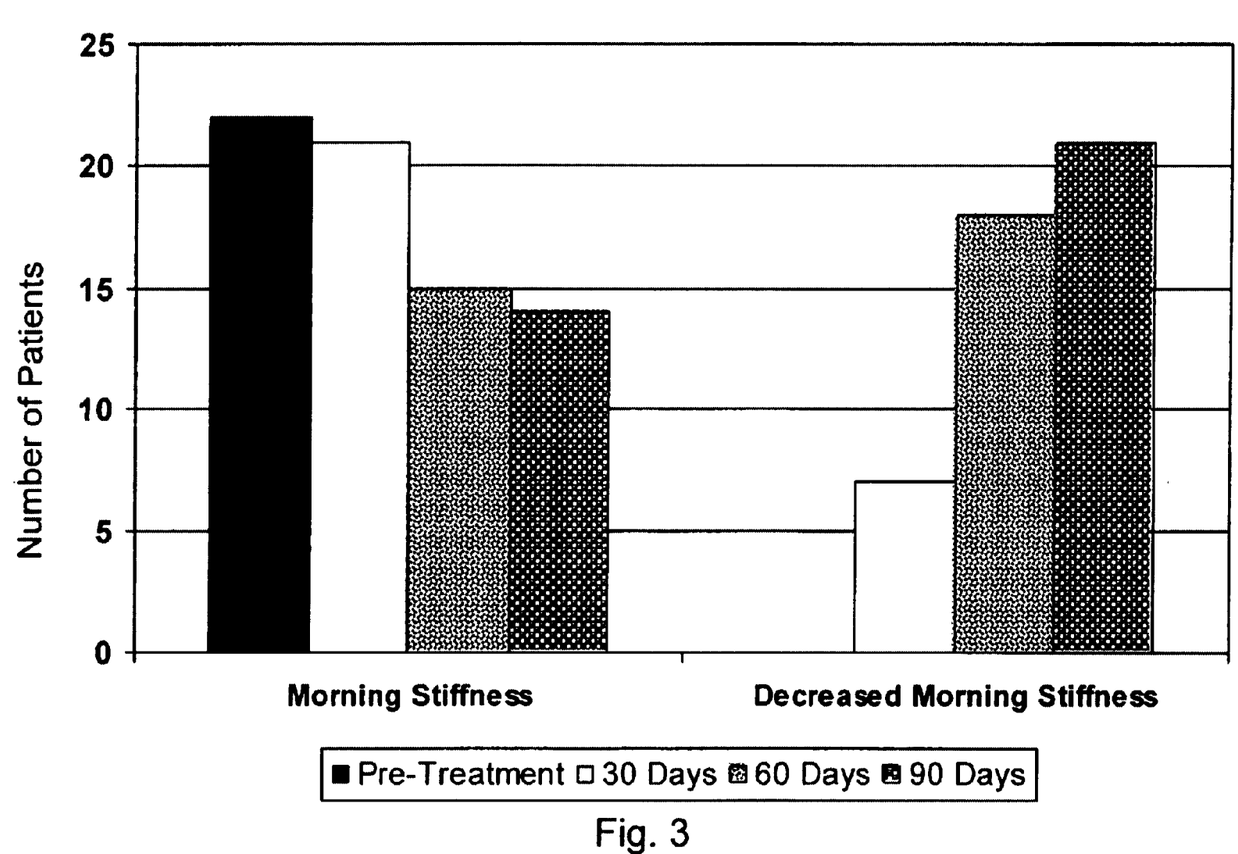
FIG. 3 shows the reduction of morning stiffness resulting from Product R treatment.

FIG. 3 shows the reduction of morning stiffness resulting from Product R treatment. Of the 28 patients, 22 had morning stiffness, which in 15 patients lasted 15 minutes or more before the Product R treatment. By day 30, one of the 22 patients reported no morning stiffness, and seven reported a reduction of morning stiffness. By day 60, an additional five patients had no morning stiffness and a total of 15 patients had a reduction of morning stiffness. By day 90, a total of 15 patients had no stiffness as compared to 6 before the treatment. 12 patients remained with morning stiffness of 15 minutes or less. One patient remained with morning stiffness of more than 15 minutes.

Figure 4A:
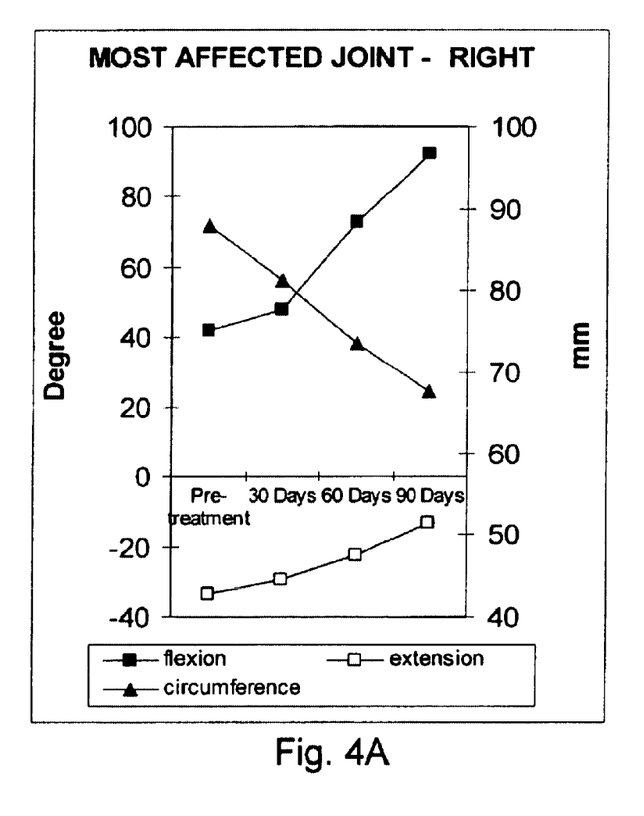
FIGS. 4A–B show the mobility of the most affected joints before and after the treatment with Product R.
Figure 4B:
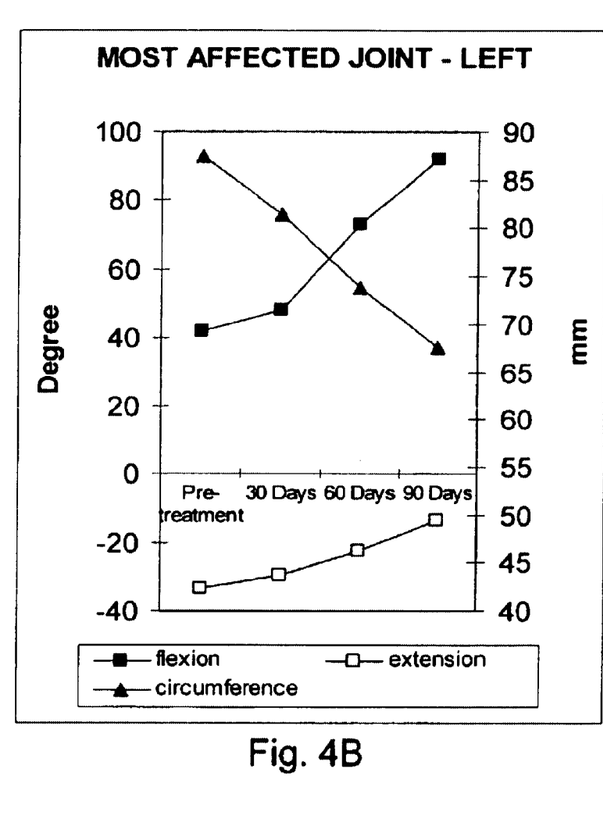

FIG. 4 shows the mobility of the most affected joints before and after the treatment with Product R. Mobility was measured by degrees of flexion and extension of the joint. All 28 patients had impaired mobility of the joints. Most patients had affected joints in hands and three patients included impaired feet joints. Flexion ranged from 30 to 50 degrees with the remainder ranging form 80 to 110 degrees. In most cases it took 60 days to see a marked improvement. At that point the improvement became exponential.

As a measurement of inflammation, the circumference in millimeters of the most affected joint was recorded. All 27 patients experienced a marked decrease in joint sizes. These decreases were visible in all cases by day 30. The reduction of the circumference of the most affected joint is also shown in FIG. 4.

Figure 5:
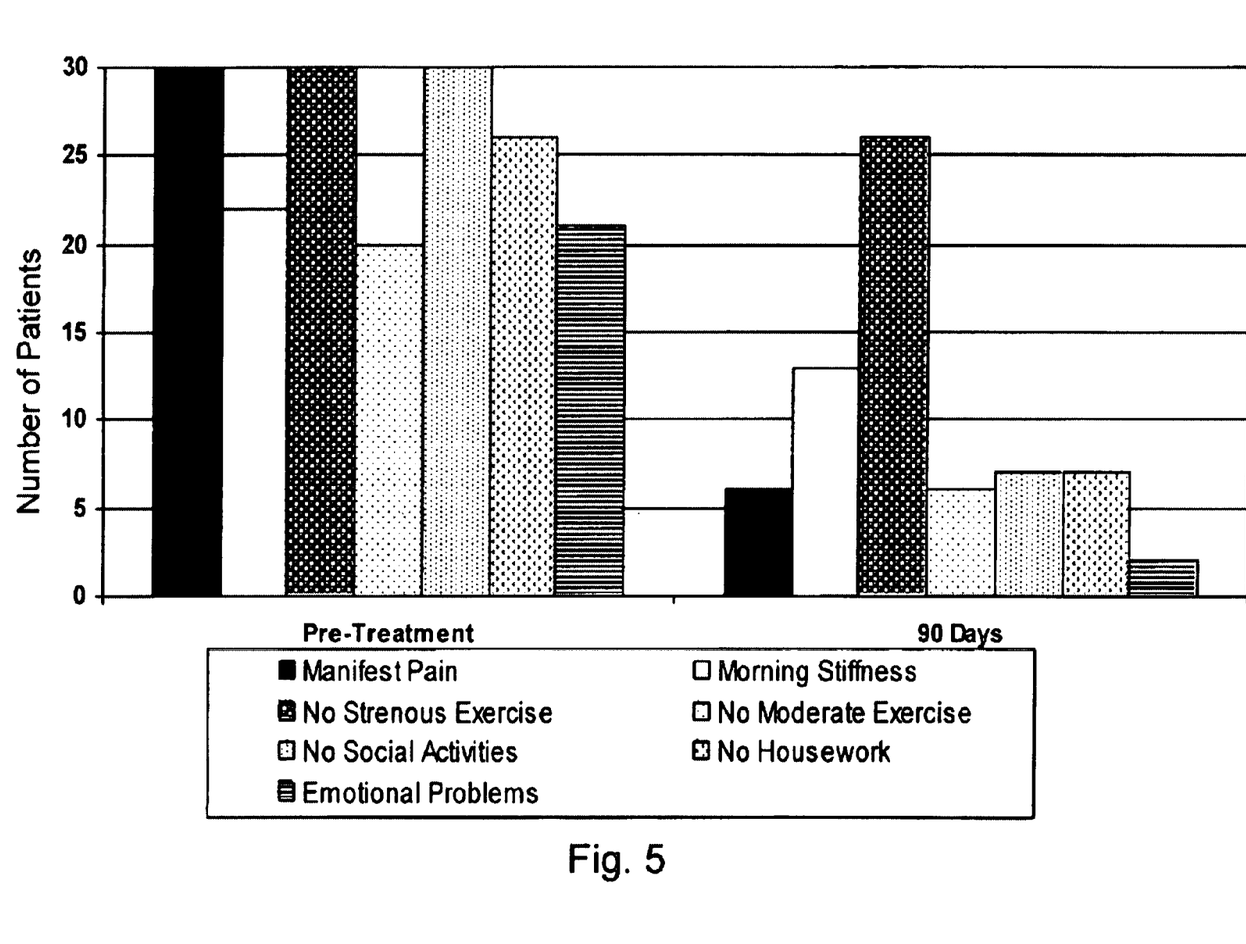
FIG. 5 shows the improvements of various activities that were hindered by rheumatoid arthritis.

FIG. 5 shows the improvements of various activities that were hindered by RA. These activities include:
Strenuous exercise:

Before Prod uct R therapy, all 27 patients were limited in their ability to perform strenuous exercises such as running, lifting heavy objects or participation in exhausting sports. 16 patients considered themselves extremely limited and 12 moderately limited. By day 90 of the therapy, two patients reported not being limited at all, 17 were moderately limited and eight still were very limited in their ability to p&form strenuous exercise.
Moderate exercise:

19 patients out of the 27 patients considered themselves to be moderately limited in their ability to perform moderate exercises such as moving a table, pushing a vacuum cleaner, bowling or playing golf By day 90, only six patients were limited in performing moderate exercises.
Job/Housework:

27 patients had problems performing their job or housework at the beginning of the study. By day 90, only seven still bad problems but to a much lower degree in all cases.
Social activities:

27 patients had some disability in performing social activities due to their illness at the beginning of the treatment. By day 90, only six still reported problems but all improvements from the pretherapy state.
Emotional problems:

21 patients reported emotional problems due to their disease at the start of the therapy. By day 90, only two still reported emotional problems and both reported improvement resulting from Product R therapy. In addition to the above observations, all patients' blood samples were collected and subjected to standard clinical laboratory tests which are designed for diagnosis and treatment of rheumatoid arthritis and performed routinely by persons of ordinary skill in the art. The results of these tests are summarized in Table I.

TABLE I

| Patient | HB (mg/ml) | | ESR (mm) | | Latex Fixation Test (IU/ml) | | | | Rose Ragan Test (IU/ml) | | | |
|---|---|---|---|---|---|---|---|---|---|---|---|---|
| | Day 0 | Day 90 | Day 0 | Day 90 | Day 0 | | Day 90 | | Day 0 | | Day 90 | |
| 1 | 14.4 | 14.1 | 38 | 26 | + | 30 | + | 30 ++ | 32 | + | 8 | |
| 2 | 13.6 | 14.2 | 32 | 26 | + | >40 | + | 30 | >8 | + | 8 | |
| 3 | 14.3 | 13.8 | 27 | 20 | ++ | 60 | + | 30 ++ | 32 | + | 8 | |
| 4 | 14.0 | 13.8 | 29 | 19 | ++ | 60 | + | 30 +++ | 128 | ++ | 32 | |
| 5 | 13.6 | 14.3 | 32 | 20 | ++ | 60 | + | 30 ++ | 32 | + | 8 | |
| 6 | 14.2 | 13.8 | 29 | 18 | ++ | 60 | ++ | 60 ++ | 32 | + | 8 | |
| 7 | 12.0 | 13.3 | 32 | 19 | ++ | 60 | + | 30 +++ | 128 | + | 8 | |
| 8 | 14.0 | 13.8 | 27 | 16 | + | 30 | + | 30 ++ | 32 | + | 8 | |
| 9 | 13.4 | 14.0 | 36 | 22 | +++ | 120 | + | 30 ++++ | 512 | + | 8 | |

TABLE I-continued

| | HB (mg/ml) | | ESR (mm) | | Latex Fixation Test (IU/ml) | | | | Rose Ragan Test (IU/ml) | | | |
|---|---|---|---|---|---|---|---|---|---|---|---|---|
| Patient | Day 0 | Day 90 | Day 0 | Day 90 | Day 0 | | Day 90 | | Day 0 | | Day 90 | |
| 10 | 13.8 | 14.3 | 29 | 15 | ++ | 60 | + | 30 | ++ | 32 | + | 8 |
| 11 | 14.0 | 13.8 | 28 | 19 | ++ | 60 | + | 30 | ++ | 32 | + | 8 |
| 12 | 13.5 | 14.3 | 26 | 14 | ++ | 60 | + | 30 | ++ | 32 | + | 8 |
| 13 | 13.6 | 14.3 | 34 | 19 | +++ | 120 | + | 30 | ++ | 32 | + | 8 |
| 14 | 12.0 | 13.0 | 27 | 17 | +++ | 120 | + | 30 | +++ | 128 | + | 8 |
| 15 | 11.3 | 12.7 | 20 | 13 | + | 30 | − | — | + | 8 | + | 8 |
| 16 | 13.8 | 14.4 | 26 | 18 | ++ | 60 | + | 30 | +++ | 128 | + | 8 |
| 17 | 12.7 | 13.6 | 27 | 14 | +++ | 120 | + | 30 | +++ | 128 | + | 8 |
| 18 | 12.6 | 13.8 | 29 | 18 | ++ | 60 | + | 30 | +++ | 128 | + | 8 |
| 19 | 13.7 | 14.8 | 31 | 17 | + | 30 | + | 30 | + | 8 | + | 8 |
| 20 | 13.6 | 14.2 | 27 | 16 | + | 30 | + | 30 | + | 8 | + | 8 |
| 21 | 12.6 | 13.9 | 25 | 14 | +++ | 120 | + | 30 | +++ | + | 8 | |
| 22 | 13.4 | 13.9 | 31 | 19 | ++ | 60 | + | 30 | ++ | 32 | + | 8 |
| 23 | 12.8 | 14.2 | 25 | 14 | ++ | 60 | + | 30 | +++ | 128 | + | 8 |
| 24 | 14.0 | 13.7 | 27 | 15 | +++ | 120 | + | 30 | +++ | 128 | + | 8 |
| 25 | 14.4 | 14.8 | 22 | 16 | ++ | 60 | + | 30 | ++ | 32 | + | 8 |
| 26 | 13.9 | 14.1 | 31 | 19 | +++ | 120 | + | 30 | +++ | 128 | ++ | 32 |
| 27 | 13.7 | 14.3 | 23 | 17 | ++ | 60 | + | 30 | ++ | 32 | + | 8 |

20 patients out of 27 had slight increases of hemaglobulin (Hb) values after 90 days of the treatment as compared with pretreatment values. The rest either remained the same or had slight decreases.

All 27 patients had lower values of erythrocyte sedimentation rate (ESR) on day 90 compared with their corresponding pretreatment values. The avenge decrease was 10.74 mm with the maximum being 15 mm and the minimum 6 mm.

All 27 patients had positive latex fixation test before the treatment, On day 90 after the start of the treatment, of the 27 patients, 22 had decreased values compared with their corresponding pretreatment values. The other five remained the same: one moderately positive (++, 60 IU/ml) and four low positive; (+, 30 IU/ml). Only one patient, who had a low positive value to start with (+, 30 IU/ml), became negative to the latex fixation test. The rest, whose values ranged from 30 to 120 IU/ml all became low positives (+, 30 IU/ml).

All 27 patents had positive Rose Ragan tests before the treatment. None of them became negative but 24 patients showed decreases of the positive values and three remained at the minimum positive value (+, 8 IU/ml) with which they started 21 patients lowered their values to 8 IU/ml including eight patients who started with high positive values of 128 IU/ml. Three patients lowered their values to 32 IU/ml, two of whom started with 128 IU/ml and one had a very high value of 512 IU/ml before the treatment.

Thus, while there have been shown and described and pointed out fundamental novel features of the invention as applied to preferred embodiments thereof, it will be understood that various omissions and substitutions and changes in the form and details of the operation illustrated may be made by those skilled in the art without departing from the spirit of the invention. For example, it is expressly intended that all combinations of those elements and/or method steps which perform substantially the same function in substantially the same way to achieve the same results are within scope of the invention. It is the intention, therefore, to be limited only as indicated by the scope of the claims appended, hereto.

The invention is not limited by the embodiments described above which are presented as examples only but can be modified in various ways within the scope of protection defined by the appended patent claims.

I claim:

1. A method of ameliorating a symptom of rheumatoid arthritis in a patient suffering from rheumatoid arthritis, comprising parenterally administering to said patient an effective symptom ameliorating amount of Product R in a range from about 2.5 microliters to about 40 microliters per kilogram of body weight per day in a pharmaceutically acceptable formulation.

2. The method of claim 1 wherein said Product R is administered in a range from about 5 microliters to about 25 microliters per kilogram of body weight per day.

3. The method of claim 1 wherein said Product R is administered in amount of about 7.5 microliters per kilogram of body weight per day.

4. A method of ameliorating a symptom of rheumatoid arthritis in a patient suffering from rheumatoid arthritis, comprising the steps of:
   a. parenterally administering Product R to said patient an elective symptom ameliorating amount of about 1 ml twice per day in a pharmaceutically acceptable formulation for about 15 days; and
   b. parenteraly administering Product R to said patient an effective symptom ameliorating amount of about 1 ml once per day in a pharmaceutically acceptable formulation for about 75 days after step a.

* * * * *